United States Patent [19]

Ota et al.

[11] 4,355,977
[45] Oct. 26, 1982

[54] CORDLESS HANDPIECE FOR DENTAL TREATMENT

[75] Inventors: Sadayasu Ota, Kyoto; Takeo Uchiya, Oomiya, both of Japan

[73] Assignee: Kabushiki Kaisha Morita Seisakusho, Kyoto, Japan

[21] Appl. No.: 192,606

[22] Filed: Sep. 30, 1980

[30] Foreign Application Priority Data

Oct. 8, 1979 [JP] Japan .......................... 54-140098[U]

[51] Int. Cl.³ ............................................... A61C 1/06
[52] U.S. Cl. .................................... 433/131; 433/126; 310/50
[58] Field of Search ............... 433/131, 126, 129, 103, 433/114; 310/266, 50, 47

[56] References Cited
U.S. PATENT DOCUMENTS 3,109,238  11/1963  Marks ................................. 433/131
3,229,369  1/1966   Hoffmeister et al. ............... 433/126
3,902,248  9/1975   Bareth ................................. 433/129
3,942,392  3/1976   Page, Jr. et al. .................... 433/129
4,103,196  7/1978   Saito et al. .......................... 310/266
4,114,276  9/1978   Malata et al. ....................... 433/129

FOREIGN PATENT DOCUMENTS 876737   5/1953  Fed. Rep. of Germany ...... 433/126
2354082  1/1978  France ................................ 433/126
1201927  8/1970  United Kingdom ............... 433/131

Primary Examiner—Gene Mancene
Assistant Examiner—John J. Wilson
Attorney, Agent, or Firm—Koda and Androlia

[57] ABSTRACT

The disclosure relates to improvements in a cordless handpiece for dental treatment having storage batteries and an electric motor incorporated therein. The improvements are that the cutting tool is increased in cutting performance and that the replacement of a contra angle and a straight tool has been facilitated.

2 Claims, 4 Drawing Figures

FIG. 3
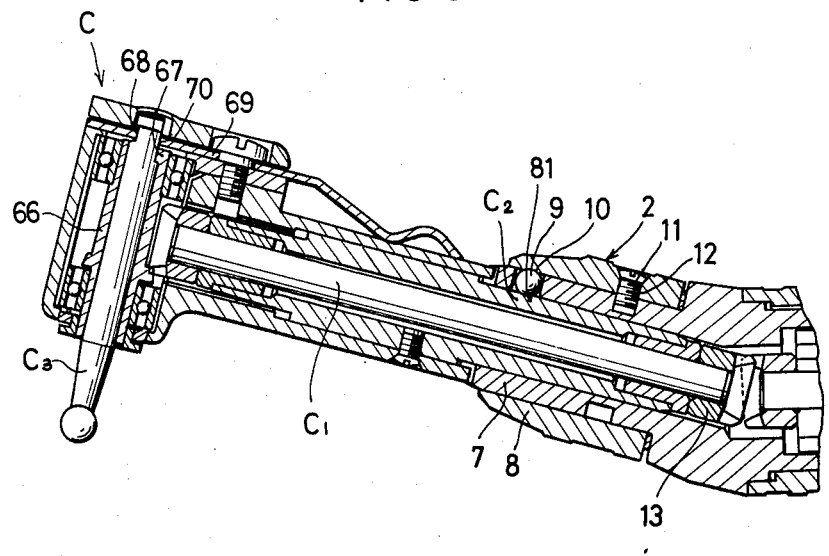
FIG. 4(a)
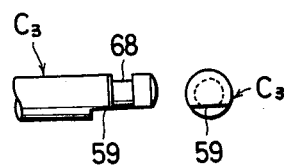
FIG. 4(b)

CORDLESS HANDPIECE FOR DENTAL TREATMENT

BACKGROUND OF THE INVENTION

1. Field of the Invention

This invention relates to a cordless handpiece for dental treatment, and more particularly to improvements in a cordless handpiece for dental treatment having a storage battery as a power source and having an electric motor incorporated thereinto.

2. Prior Art

The cordless handpiece, having storage batteries and an electric motor incorporated thereinto, is well known in Japanese Utility Model Publications Nos. 27836/72, 27837/72, 34557/72 and 24701/73, but there is a considerable gap between the anticipatability of the inventions and the development of the products now on the market. Presently, products which have cutting sharpness and in which the contra angle and straight tools are readily replaceable have not yet been industrialized. Taking this into consideration, the present inventor can point out two problematic points. One of them is a problem of the rotational characteristic of an electric motor, namely a problem related with the number of rotations and rotational torque. The other problem relates to the construction to mount a detachable contra angle and straight tool on the handpiece. The difficulty in solving the first problem is in general practice conventional use of a cored motor produces magnetic reluctance in the gap between a stator and a rotor. The reluctance, in turn, acts on the widening of each slot and produces reluctance torque to thereby cause a torque drop, and that discrepancy in rotation by pulsation, namely, a relatively large cogging torque [cogging torque $\approx$ (reluctance torque)+(torque by current pulsation)], makes it difficult to attain a rotational characteristic on the order of 15,000 rpm (number of rotations) and a torque of 130~150 g.cm, which is desirable for cutting teeth. When the storage battery is enlarged in size (diameter) in order to overcome the difficulty described above, the weight of an enlarged diameter handpiece grip portion makes it very inconvenient for fine and delicate operation by hand. The second problem is that it is necessary to replace the contra angle and straight tools very often, but no consideration has been given to facilitating replacement of the contra angle and straight tools in the conventional handpiece. Frequent replacement has counterbalanced, to a substantial degree, the predominant characteristics of an efficient cordless handpiece.

SUMMARY OF THE INVENTION

In the invention, the first problem has been solved by the obtainment of the described rotational characteristic, free from reluctance torque and reduced in cogging torque by the use of a coreless motor so as to make the rotational characteristic lower in inertia and adaptive for repetition of high-speed starting and stopping necessary for dental treatment. The second problem has been solved by development of a joint which makes it very easy to detachably mount either a contra angle tool or a straight tool with the tools left attached to the handpiece body.

A preferred embodiment of the invention will now be described with reference to the accompanying drawings:

BRIEF DESCRIPTION OF THE DRAWINGS

In the drawings:

FIG. 3 is an enlarged sectional front view showing the inside of the contra angle tool at the tip of the handpiece of FIG. 1; and FIG. 4 shows a front view (a) and a side view (b) of a tool bar for combined use in the straight and the contra angle tools.

DETAILED DESCRIPTION OF THE INVENTION

Figure 1:
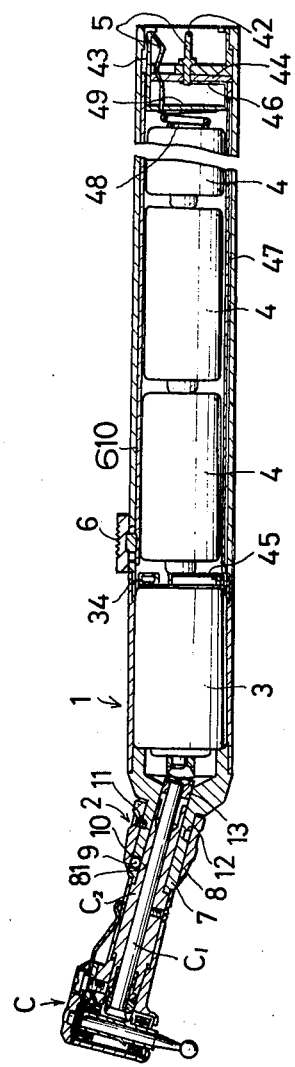
FIG. 1 is a longitudinal sectional front view of a preferred embodiment of the handpiece according to the invention wherein a contra angle tool is used.

In FIG. 1, the numeral 1 designates a handpiece body which is equipped at its tip portion with a hollow sleeve 7 fitted over the circumference of a housing $C_2$ of a contra angle tool C. At the tip of the handpiece body 1 is provided a joint 2 so as to permit a straight tool S or a contra angle tool C to be detachably replaced. Stated more concretely, the joint 2 comprises a set sleeve 8 rotatably sleeved over the sleeve 7, a ball groove 81 provided at one point of the sleeve 7 circumferentially thereof and passing through the thickness of the sleeve 7, a locking ball 9 nesting in the groove 81 and abutting at the lower end against the housing $S_3$ of the straight tool S or the housing $C_2$ of the contra angle tool C, an eccentric groove 10 corresponding to the locking ball 9 and provided in the circumference of the set sleeve 8, and a set screw 11 passing through the thickness of the sleeve 8 and set in the thickness of the sleeve 7. By this eccentric groove 10 is meant a groove gradually shallow in the bottom circumferentially of the inner circumference of the set sleeve 8. The ball groove 81 is circumferentially uniform in diameter. The locking ball 9 is generally made of steel. A screw groove 12 is formed in the range of approximately 180° of the outer circumference of the sleeve 7 in order to receive the set screw in the thickness of the sleeve 7 and the set screw 11 is screwed into the groove 12 within the range of the groove so as to lock the set screw against rotation. In other words, so as to permit the free detachment of the contra angle tool C or the straight tool S by rotation of the sleeve 8 within the range of rotation of about 180°. The numeral 3 designates a coreless motor housed in the handpiece body 1 and connected through a transmission gear 13 to a driving shaft $S_1$ of the straight tool S or to a driving shaft $C_1$ of the contra angle tool C, and 4 designates storage batteries functioning as a power source of the motor 3, the batteries being shown provided in three batteries 4. The batteries 4 . . . are housed in the handpiece. The coreless motor 3 is a motor having no rotor (core), but which includes a rotor conductor and a nonmagnetic insulator which transmits rotation and in which, when a direct current (I . . . Amp) is flowed through a stator coil conductor of a length (l . . . m) in the magnetic field a magnetic flux density (B . . . Wb/m²) generated from a field magnet of a stator, the rotor and the coil conductor produce a force of B·l·I·(N). As the storage batteries are used three Ni-Cd batteries each having an output of 1.2 v and having a gross output voltage of 3.6 v. The rotational characteristic of the motor 3 using the batteries in about 15,000 rpm (number of rotations) and 130 150 g.cm in torque, and the normal cutting performance necessary for cutting teeth is achieved in the range of this rotational characteristic. A switch 6 is a general slide switch which turns on and off the negative pole 34 of the motor 3 and the negative pole piece 43 of the battery 4 by sliding a slide piece 610. Since the continuous duty time of the batteries 4 . . . is about one hour and a half, for maintenance of the described characteristic of rotation, the handpiece body 1 is provided inside of the distal end thereof with a charging electrode 5 shown in FIG. 1 so as to permit charging by connecting the body 1, when not in use, to a charger not shown. Namely, the charging electrode 5 comprises a positive pole pin 42 protrudently provided and a negative pole piece 43 provided inside the rear end of the handpiece body 1, an insulating wall 44 insulatively holding both the pin and the piece, conductive pieces 46 and 47 connecting the pin 42 to the positive pole terminal 45 of the battery 4, and a conductive piece 49 connecting the negative pole piece 43 to the negative pole coiled spring 48 of the battery 4. It will be understood from the handpiece, constructed in the manner described, that insertion of the distal end of the handpiece body 1 into a charger (not shown) charges both the positive and negative poles of the batteries . . . .

The charging electrode 5, shown by way of example, is not limited to the embodiment illustrated. The straight tool S and contra angle tool C shown can utilize a single tool bar. In this case, there is provided in the straight tool S a tool holding structure in which the tool bar $C_3$ for use in the contra angle tool C, shown in FIGS. 4(a) and 4(b), can be used also in the tool bar for use in the straight tool S. These tool bars as described with reference to FIGS. 2, 3, 4(a) and 4(b). In the straight tool S in FIG. 2, the tool bar $S_2$, used therein, is a conventional contra angle tool bar, namely as shown in FIG. 4(a) and 4(b), provided at the terminal end with an engagement portion 59 formed by a cutout portion.

Figure 2:
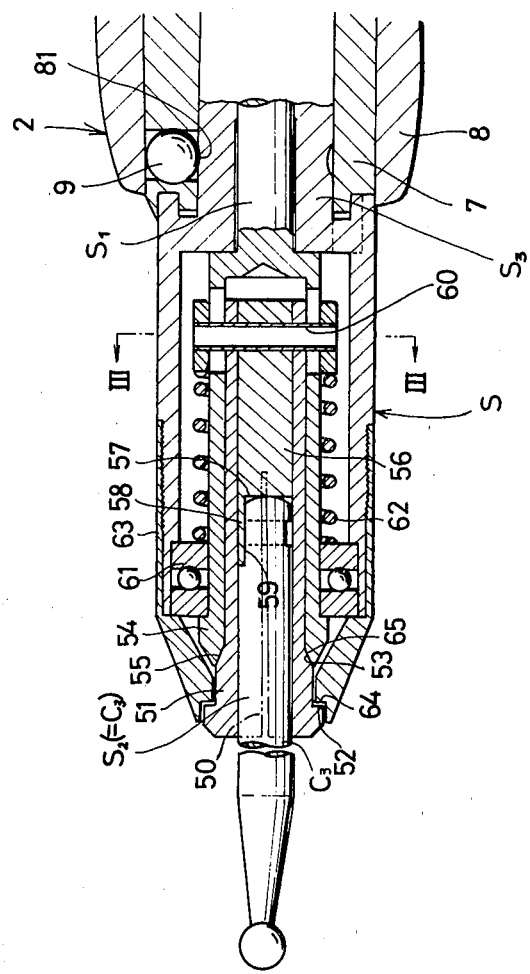
FIG. 2 is an enlarged longitudinal sectional front view of another embodiment of the invention wherein a straight tool is used.

The tool holding structure of the tool bar $S_2$ is constructed in the following manner. In FIGS. 2 and 3, on the outer circumference of the tip of the tool bar holding cylinder 51, having eleasticity imparted thereto by forming slits 50 in the cylinder along the lengthwise extension thereof, is formed a stepped portion 52 for engagement. A sloping surface 53 is formed in the reduced portion of the rear portion of the stepped portion 52, and a rotating tube shaft 54 is fitted over the tool bar holding cylinder 51. A sloping surface 55, always in contact with the sloping surface 53, is formed on the inner circumference of the shaft 54 at the tip thereof, and a connecting bar 56 is inserted into the cylinder 51 in the rear portion thereof. A receptive portion 57 is formed by cutting out the tip of the connecting bar 56, an engaging tongue member 58 is protrudently provided at the tip of the receptive portion 57, so as to be engated with an engagement portion 59 formed on one side of the rear portion of the bar $C_3$, for exclusive use in the contra angle tool inserted into the cylinder 51. The cylinder 51 is connected by a knock pin 60 with the rotating tube shaft 54 and connecting bar 56, and on the outer circumference of the tube shaft 54 are mounted a ball bearing means 61 and a compression spring means 62 in such a manner so as to surround the shaft 54. A cap 63 is detachably provided outwardly of the ball bearing means 61 so as to bring the stepped portion 64, provided on the inner circumference of the cap 63 at the tip thereof into an opposed relation with the stepped portion 52 and to elastically press the sloping surface 65 against the sloping surface 53 by the ball bearing means 61 and the spring means 62.

Since the tool holding structure of the embodiment in FIG. 2 is of the described construction, insertion of the tool bar $S_2$, i.e. bar $C_3$ for exclusive use in conta angle tool into the tool bar holding cylinder 51, makes it possible to hold the bar $C_3$ because of the fact that the cylinder 51 is provided at the tip with several slits 50 so as to impart elasticity to the cylinder 51 and the fact that the cylinder 51 is provided on the outer circumference at the tip thereof with the engagement stepped portion 52 and the sloping surface 53 and the sloping surface 55 formed on the inner circumference of the tube shaft 54 at the tip thereof is pressed against the surface 54 by the ball bearing means 61 and the resilience of the compression spring means 62 mounted on the shaft 51 so as to contrast the tip of the cylinder 51 convergently to hold the bar $C_3$. Thus, the holding structure of the kind described provides the advantage that, along with the contraction of the tip of the cylinder 51 and the provision of the connection cylinder 56 inside the cylinder 51 in the position capable of exposing the cylinder 56 to a length about two-fifths of the length of the bar $C_3$, the tool bar $C_3$ for exclusive use in contra angle tool can be inserted into and held in the tool bar cylinder 51 for a straight handpiece, making it possible to dispense with a tool bar for a straight handpiece. And when it is desired to draw the bar $C_3$ from the tool bar holding cylinder 51, it is only necessary to move the cap 63 to the left, bring the stepped portion 64 into engagement with the engagement stepped portion 52, move the tool bar cylinder to the left, move the sloping surface 53 away from the sloping surface 65, loosen grip of the cylinder 51 upon the bar $C_3$ and draw the same.

Incidentally, the substance of the invention described above is disclosed in detail in the specification and drawings of Japanese Patent Application No. 075655/1978 filed by K. K. Morita Tokyo Seisakusho, associated company of the present applicant. On the other hand, since the tool holding structure inside the contra angle tool C is the same as the conventional one, a detailed description thereof is omitted. Referring very briefly to FIG. 3, the engagement portion 59 of the tool bar $C_3$ is brought into engagement with an inwardly projecting stepped portion 67 at the distal end of a rotor so as to prevent rotation of the bar $C_3$ and a circular groove 70 of a bar latch 69 is fitted into the circumferential groove 68 of the bar $C_3$ to prevent the bar $C_3$ from being axially drawn out. As described, the use of the tool bar $C_3$ also in combination with the straight tool bar $S_2$ relieves an operator of the trouble of replacing bars by selecting each separate bar.

Since the invention is constructed as described above, the power supply of the batteries 4 . . . to the coreless motor by operation of the switch 6 makes it possible not only to impart rotation having the described characteristic of rotation adapted for dental treatment to a straight tool driving shaft $S_1$ or a contra angle tool driving shaft $C_1$ and to make a cutting operation, but also to dispense with such storage batteries as necessitated by an enlarged diameter of the grip of the handpiece. Furthermore, the invention greatly facilitates attachment and detachment of the straight tool S and contra angle tool C. Namely, by loosening a set screw 11 with the set screw left inserted into a screw groove 12 and rotating a set sleeve 8 in the direction of an eccentric groove 10 getting deeper releases a locking ball 9. For example, diametrically from the outer circumference of a housing C₂ of the contra angle tool C and then drawing off the housing axially can provide ready detachment of the straight tool S and contra angle tool C. Furthermore, for example, when the housing S₃ of the straight tool is inserted into the joint 2 and first the set sleeve 8 is reversely rotated to press the locking ball 9 against the circumference of the housing S₃ and then the set screw 11 is screwed down, and the housing is firmly held by the joint 2.

As described above, the invention makes it possible to attach and detach the straight tool S or contra angle tool C with the joint 2 left mounted on the handpiece body 1, and accordingly, the invention greatly improves the work efficiency of the operator and produces a positive effect on the treatment operation in comparison with the conventional handpiece body, wherein the straight tool or contra angle tool had to be detached every time and wherein the same was thereafter attached again.

Although small in size, the handpiece of the invention provides the described characteristic of rotation necessary for cutting by the application of the coreless motor 3. The high efficiency of the handpiece of the invention will further be increased by the combined use of a straight tool having a tool holding structure capable of using the tool bar for a contra angle tool described and shown also in the straight tool.

I claim:

1. A cordless handpiece for dental treatment with replacement contra angle and straight tools, comprising a joint mounted on the tip portion of a handpiece body so as to replaceably attach and detach a straight tool or a contra angle tool to and from the tip portion, a coreless motor housed in said handpiece body and connected directly to a driving shaft of said straight tool or to a driving shaft of said contra angle tool, storage battery housed in said handpiece body for driving said coreless motor, an electrode likewise housed in the distal end of said handpiece body for charging said batteries and a switch for controlling turning on and off said motor, wherein said motor, batteries and electrode are located on the same axis and said joint comprises a set sleeve fitted rotatably over a sleeve at the tip portion of said handpiece body, a ball groove provided at one end of said sleeve circumferentially of the sleeve passing through the thickness of said sleeve, a locking ball nesting in said groove and adapted to bring the lower end thereof into abutment against the housing of said straight tool for the housing of said contra angle tool, an eccentric groove corresponding to said locking ball and formed on the inner surface of said sleeve, and a set screw passing through the thickness of said sleeve and set in the thickness of said sleeve whereby said contra angle and straight tools are readily replaceable by loosening said set screw and rotating said set sleeve.

2. A handpiece according to claim 1, wherein said straight tool includes an engagement stepped portion formed on the outer circumference of a tool bar holding cylinder at the tip of the cylinder by forming slits therein along the lengthwise extension thereof so as to impart elasticity to the cylinder, a sloping surface formed in the reduced portion rearwardly of said engagement stepped portion, a rotating tube shaft fitted over said tool bar holding cylinder, a sloping surface always in contact with said sloping surface formed on the inner circumference of said rotating tube shaft at the tip of the shaft, a connecting bar inserted into the rear portion of said cutting bar holding cylinder, a receptive portion formed by cutting off the tip of said connecting bar, an engaging tongue member portrudently provided at the top of said receptive portion, said engaging tongue member being formed so as to enable the tongue member to engage with an engagement portion formed on one side of the rear part of tool bar for exclusive use in a contra angle tool inserted into said tool holding cylinder, a knock pin by which to connect said rotating tube shaft and connecting bar integrally to said cylinder, a ball bearing means and a compression spring means mounted on the outer circumference of said tube shaft, and a cap being provided outwardly of said ball bearing so as to move back and forth freely and bring the stepped portion formed on the inner circumference of said cap at the tip of the cap in opposition with said engagement stepped portion and support said sloping surface resiliently by said sloping surface by means of said bearing means and said compression spring means.

* * * * *